(12) United States Patent
Basu et al.

(10) Patent No.: US 6,597,756 B1
(45) Date of Patent: Jul. 22, 2003

(54) METHODS AND APPARATUS FOR MULTI-SLICE IMAGE RECONSTRUCTION

(75) Inventors: Samit K. Basu, Niskayuna, NY (US); Jiang Hsieh, Brookfield, WI (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 10/176,427

(22) Filed: Jun. 19, 2002

(51) Int. Cl.$^7$ ................................................ A61B 6/03
(52) U.S. Cl. ............................ 378/15; 378/8; 378/901
(58) Field of Search .............................. 378/4, 8, 15, 94

(56) References Cited

U.S. PATENT DOCUMENTS

| | | |
|---|---|---|
| 5,187,659 A | * 2/1993 | Eberhard et al. .............. 378/9 |
| 5,396,528 A | 3/1995 | Hu et al. |
| 5,448,607 A | 9/1995 | McKenna |
| 5,541,971 A | 7/1996 | Saito |
| 5,673,300 A | 9/1997 | Reckwerdt et al. |
| 5,682,414 A | 10/1997 | Saito |
| 5,812,628 A | 9/1998 | Hsieh |
| RE36,415 E | 11/1999 | McKenna |
| 6,115,447 A | 9/2000 | Hsieh |
| 6,256,369 B1 | 7/2001 | Lai |
| 6,359,958 B2 | 3/2002 | Toth |

* cited by examiner

Primary Examiner—David V. Bruce
(74) Attorney, Agent, or Firm—Carl B. Horton, Esq.; Armstrong Teasdale LLP

(57) ABSTRACT

A method for acquiring views of an object includes acquiring a first quantity of views at a first position on a z-axis, acquiring a second quantity of views different from the first quantity at a second position on the z-axis different from the first position, and acquiring a third quantity of views equivalent to the first quantity at a third position on the z-axis different from the first position and the second position. A method is also described for processing these views to reconstruct the object.

27 Claims, 5 Drawing Sheets

US 6,597,756 B1

METHODS AND APPARATUS FOR MULTI-SLICE IMAGE RECONSTRUCTION

BACKGROUND OF THE INVENTION

This invention relates to computed tomographic (CT) imaging, and more particularly to methods and apparatus for reducing imaging artifacts an image generated using a multi-slice CT imaging system.

With the introduction of new X-ray source technologies into the CT field, a number of new reconstruction challenges have arisen. In particular, addressable field-array emitters and electron-beam sources (such as are in the "inverted cone" trajectory) lead to somewhat non-traditional data acquisition techniques, and therefore require reconstruction algorithms for use with the addressable field-array emitters and electron-beam sources.

BRIEF DESCRIPTION OF THE INVENTION

In one aspect, a method for acquiring views of an object is provided. The method includes acquiring a first quantity of views at a first position on a z-axis, acquiring a second quantity of views different from the first quantity at a second position on the z-axis different from the first position, and acquiring a third quantity of views equivalent to the first quantity at a third position on the z-axis different from the first position and the second position.

In another aspect, a computer for acquiring views of an object is provided. The computer is programmed to acquire a first quantity of views at a first position on a z-axis, acquire a second quantity of views different from the first quantity at a second position on the z-axis different from the first position, and acquire a third quantity of views equivalent to the first quantity at a third position on the z-axis different from the first position and the second position.

In a further aspect, a computed tomographic (CT) imaging for acquiring views of an object is provided. The CT system includes a detector array, at least one radiation source, and a computer coupled to the detector array and the radiation source and configured to acquire a first quantity of views at a first position on a z-axis, acquire a second quantity of views different from the first quantity at a second position on the z-axis different from the first position, and acquire a third quantity of views equivalent to the first quantity at a third position on the z-axis different from the first position and the second position.

In a still further aspect, a method for reconstructing an image of an object is provided. The method includes acquiring a plurality of circle trajectories wherein each circle trajectory includes a plurality of views and generating a single reconstruction for each of the acquired circle trajectories.

DETAILED DESCRIPTION OF THE INVENTION

Figure 1:
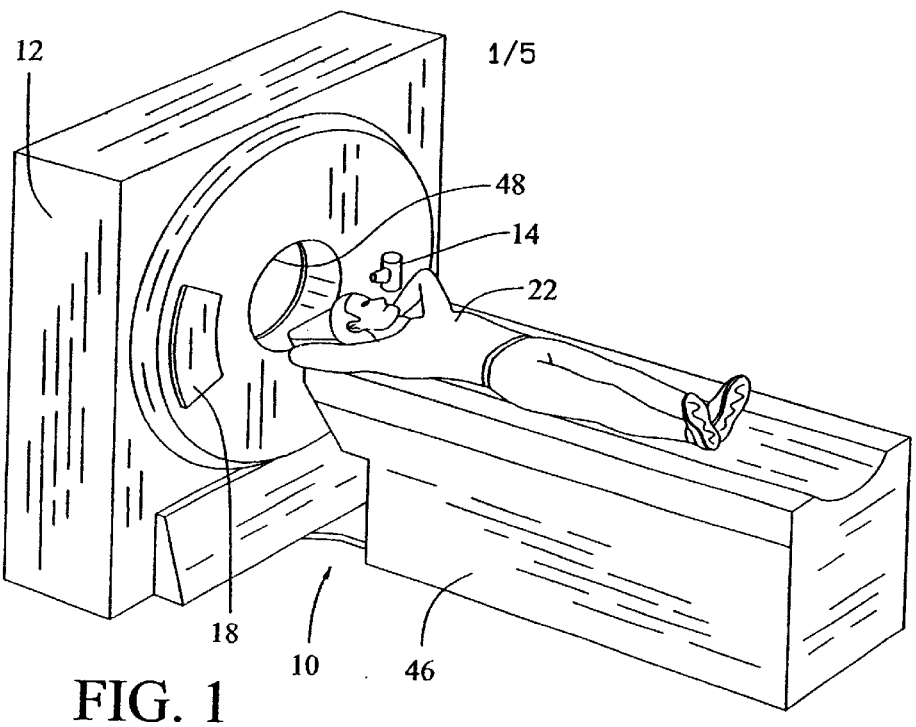
FIG. 1 is a pictorial view of a CT imaging system.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam attenuation at the detector location. The attenuation measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The helical weighting algorithms also scale the data according to a scaling factor, which is a function of the distance between the x-ray source and the object. The weighted and scaled data is then processed to generate CT numbers and to construct an image that corresponds to a two dimensional slice taken through the object.

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 2:
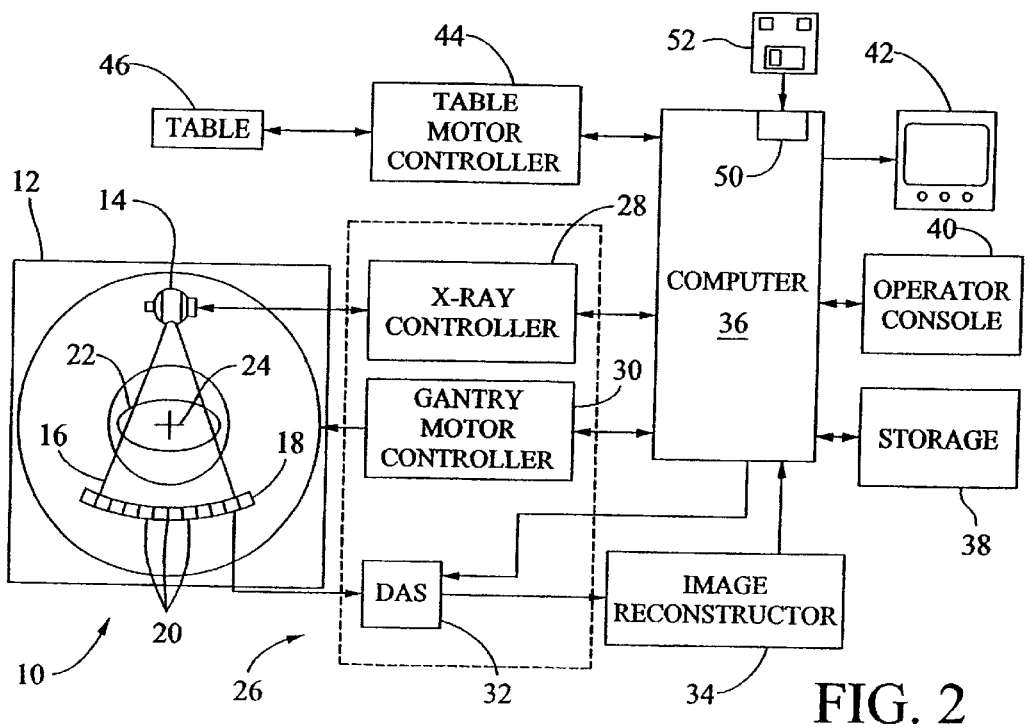
FIG. 2 is a block schematic diagram of the system illustrated in FIG. 2.

Referring to FIGS. 1 and 2, a multi-slice scanning imaging system, for example, computed tomography (CT) imaging system 10, is shown as including a gantry 12 representative of a "third generation" CT imaging system. Gantry 12 has an x-ray source 14 that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22. Each detector element 20 produces an electrical signal that represents the intensity of an impinging x-ray beam and hence the attenuation of the beam as it passes through object or patient 22. During a scan to acquire x-ray projection data, gantry 12 and the components mounted thereon rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits.

Figure 3:
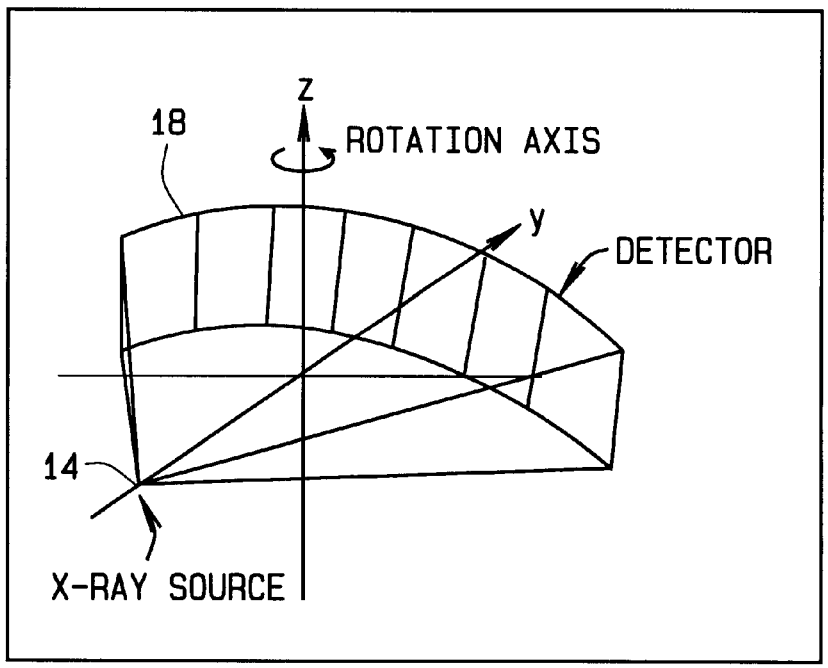
FIG. 3 is a perspective view of a known radiation source geometry.

FIG. 3 is an illustration of a standard Feldkamp, David, and Kress (FDK) geometry. Using the FDK geometry, a point radiation source 14 is positioned opposite detector 18. Detector 18 is curved along the surface of a cylinder (not shown), an axis of the cylinder is parallel to a Z-axis, and source 14 moves on the cylinder whose axis includes the Z-axis. In a general FDK acquisition, source 14 travels along a trajectory that is a circle in the X-Y plane at Z=0. However, as was demonstrated by Grangeat, this trajectory is not complete in the sense that it is impossible to exactly reconstruct an object 22 being scanned using this single dataset.

Figure 4:
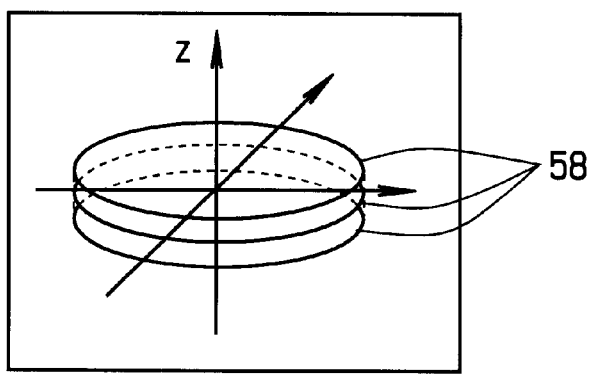
FIG. 4 is perspective view of multiple circle trajectories

FIG. 4 is an illustration of a plurality of circle trajectories 58 acquired using source 14 moving in a Z direction and rotating around a circular orbit at an angle θ. In one embodiment, a kth projection is acquired at a source position in accordance with $$[SID\ cos(\theta_k) SID\ sin(\theta_k) z_k],\quad\quad \text{Equation 1}$$

where
$z_k$ is a projection k acquired at a point on the Z axis;
SID is a source image detector; and
θ is the source angle.
A general FDK trajectory is defined as $$\theta_k = \frac{2\pi}{P}, z_i = 0 \quad\quad \text{Equation 2}$$

where
P is a quantity of views acquired for each source 14 orbit, and
$z_k$ is a projection k acquired at a point on a Z-axis.
For example, if multiple circle trajectories, i.e., a total of L circles, are acquired sequentially at different Z-locations, then the terms of the parameterization in Equation 2 can be written as $$\theta_k = \frac{2\pi k}{P}, z_k = a_1, 0 \le k < P \quad\quad \text{Equation 3}$$

$$\theta_k = \frac{2\pi(k-P)}{P}, z_k = a_2, P \le k < 2P$$

$$\vdots$$

$$\theta_k = \frac{2\pi(k-(L-1)P)}{P}, z_k = a_L, (L-2)P \le k < (L-1)P$$

wherein
k is a single view;
l is a single circle acquired at a point z on the Z-axis
L is a total quantity of circles acquired;
$\theta_k$ is a source angle when acquiring view k;
P is a quantity of views acquired for each source orbit;
$z_k$ is a projection k acquired at a point z on the Z axis; and
$a_n$ is a point on the Z axis, where n=1. . . L.

Figure 5:
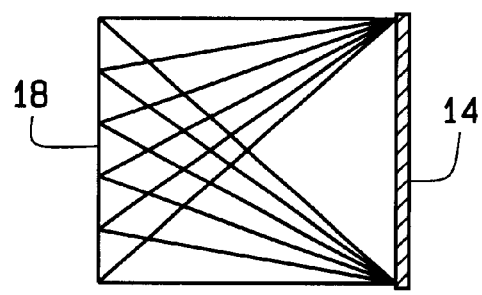
FIG. 5 is an illustration of a sampling pattern acquired with a moving source and a moving detector.
Figure 6:
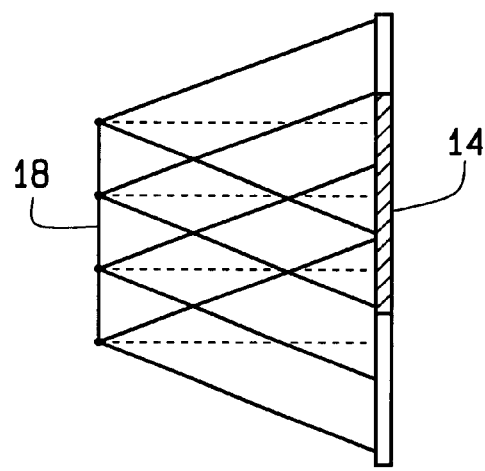
FIG. 6 is an illustration of a sampling pattern acquired with a moving source and a stationary detector.

FIG. 5 is an illustration of a sampling pattern acquired with a moving source 14 and a stationary detector 18, i.e., a center of detector 18 is fixed at Z=0, and source 14 is moving using at least one of the technologies described herein. FIG. 6 is an illustration of a sampling pattern acquired with a moving source 14 and a moving detector 18, i.e., a series of standard circle acquisitions in a "step-and-shoot" mode. In the exemplary embodiment, the movement of source 14 can be accomplished using a plurality of technologies, such as, but not limited to, a line-source, an inverted cone, and a plurality of tubes.

A reconstruction algorithm for the continuous analogue of the trajectories illustrated in FIG. 6 is constructed using a technique wherein each "circle" is treated independently and L separate reconstructions of a region of interest (ROI) is constructed, one for each Z-position of source 14. Each circle can be reconstructed using the FDK algorithm according to $$f_1(x,y,z), f_2(x,y,z), \ldots f_L(x,y,z) \quad \text{Equation 4}$$

wherein Equation 4 is referred to as component reconstructions.

Additionally, for each Z-position $a_1$, the FDK reconstruction is simplified to a fan-beam reconstruction at the plane $z=a_1$. Therefore the image quality due to the incomplete nature of the data decreases monotonically as data is acquired away from the Z plane containing source 14.

The reconstructions described above are combined using weights that vary as a function of the spatial coordinates according to $$f(x, y, z) = \sum_{1}^{L} w_l(x, y, z) f_l(x, y, z) \quad \text{Equation 5}$$

L reconstructions are combined using weights that bias the final reconstruction towards the component reconstruction corresponding to the source plane closest to a given Z location. For example, if weights are applied as a function of Z only, and the circles are equally spaced along the Z-axis in accordance with $$a_l = (l-L/2) \cdot \Delta z \quad \text{Equation 6}$$

where l is an single circle,

L is a quantity of l circles, and z is a change in the Z-axis position.

The reconstructions are combined in accordance with $$f(x, y, z) = \sum_{l=1}^{L} w(z - (l - L/2) \cdot \Delta z) f_l(x, y, z) \quad \text{Equation 7}$$

Further, if the weights satisfy an interpolation property defined as $$w(z) = \begin{cases} 1 & z = 0 \\ 0 & z = (l - L/2) \cdot \Delta a, l = 0 \ldots L - 1' \end{cases} \quad \text{Equation 8}$$

then the final reconstruction f is exact because each of the component reconstructions is exact at the appropriate z-location for those planes which contain source circles.

A weighting function that is proportional to the average (weighted average) cone angle may also be used to reconstruct the point (x,y,z). The proportional weighting function accounts for the cone angle variation as a function of (x,y). For the same z value, the cone angle reduces with the increased distance to x-ray source 14 (shown in FIG. 1).

Figure 7:
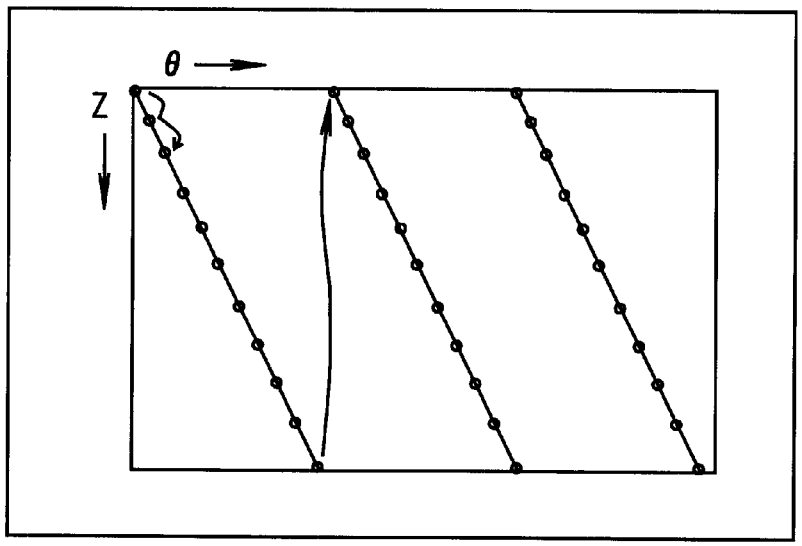
FIG. 7 is a sampling pattern acquired allowing a gantry to rotate during the-movement of the focal spot.

FIG. 7 is a sampling pattern acquired allowing gantry 12 (shown in FIG. 1) to rotate during the movement of the focal spot. The stack of circles L described previously herein is one possible sampling pattern. But to realize this acquisition pattern with a movable focal spot, the spot may be rotated about the object several times, changing the z-location with each rotation, or the spot may be scanned through the z-locations $z=a_1$ for each position θ with gantry 12 remaining stationary. If the spot is scanned through the z-locations $z=a_1$ for each position θ, and gantry 12 rotates during the-movement of the focal spot, the spot is effectively moved through the locations sequentially as shown in FIG. 7.

Assuming the time to return to a given z-location is constant, the source sampling pattern guarantees that each component reconstruction can be performed with an equal number of equally spaced views. However, this configuration suffers from two problems. First the number of rays that pass through the center of object 22 (shown in FIG. 1) is much larger than the number of rays that pass through any point on the two flat faces of the ROI. Because the final reconstruction is a weighted sum of filtered backprojections, this implies that the noise properties may be non-uniform throughout the volume. The second problem is that this same property, i.e. that the center of the volume is over-sampled, implies that the quantity of views required to obtain a given resolution is larger than is necessary to reconstruct an image of object 22 (shown in FIG. 1). In particular, the separable "stack of circles" sampling pattern shown in FIG. 7 requires L*P samples, where L is a quantity of individual circles l, and P is a quantity of views in each circle l.

For example, if 1000 views (P) are required to obtain sufficient image quality in each of the planes containing a source circle l, and there are 10 source orbits, i.e. L=10, then the total number of views required is 10,000, i.e. L*P=10,000. The total views (P) can be reduced, since many of the views passing through a center plane are redundant. With the exception of the two "faces" of the ROI, i.e. the minimum and maximum Z-locations, points in the reconstruction volume are azimuthally oversampled as a result of the large number of cross-rays passing through them. The sampling pattern can be modified to use a more complicated sampling pattern with better ray distribution properties to correct for oversampling.

Figure 8:
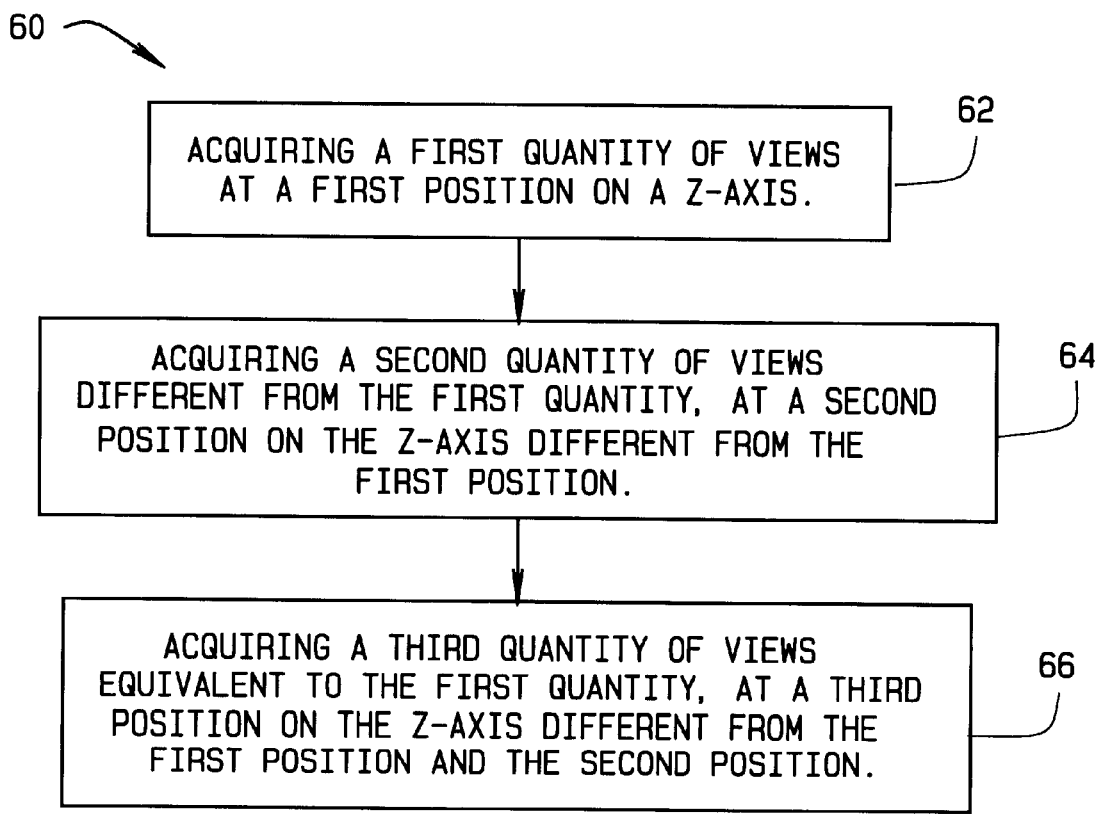
FIG. 8 is a flow diagram of a method for reconstructing an image of an object.

FIG. 8 is a flow diagram of a method 60 for reconstructing an image of an object. Method 60 includes acquiring 62 a first quantity of views at a first position on a z-axis, acquiring 64 a second quantity of views different from the first quantity at a second position on the z-axis different from the first position, and acquiring 66 a third quantity of views equivalent to the first quantity at a third position on the z-axis different from the first position and the second position.

In the exemplary embodiment, method 60 includes the following constraints, the focal spot is in exactly one (theta (θ), Z) location at any given time. Further, when separated into a plurality of component reconstructions l, each component reconstruction l is formed from views that are equally spaced on the circle in that component's plane. Additionally, each FDK reconstruction is performed with angularly equally-spaced data, and the sample distribution is controllable. In the exemplary embodiment, the sample distribution can be controlled by altering the parameters of the sampling scheme to facilitate ensuring that different ray densities are obtained inside the reconstruction volume.

Figure 9:
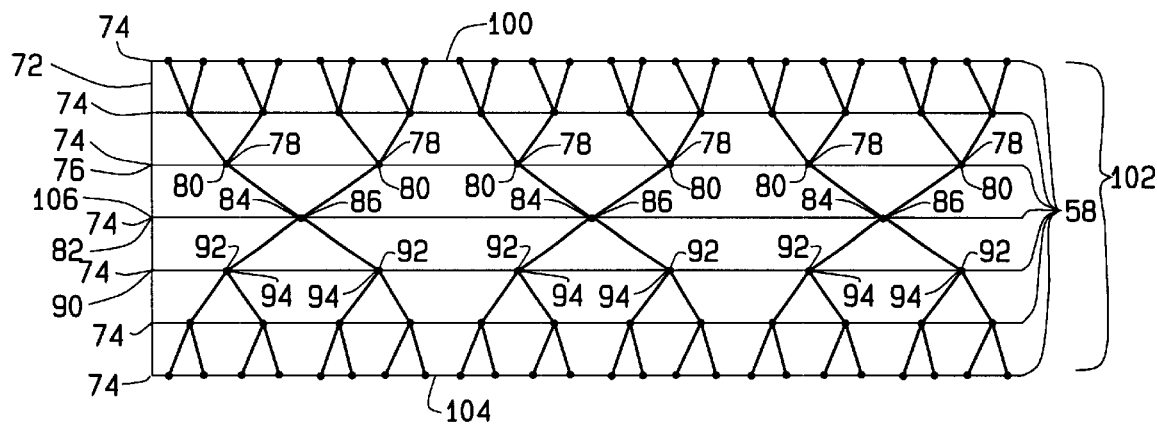
FIG. 9 is an illustration of a binary tree sampling pattern acquired using the method shown in FIG. 8.

FIG. 9 is an illustration of a binary tree sampling pattern 70 acquired using method 60. In use, radiation source 14 (shown in FIG. 1) is translatable along a Z-axis 72 to a position 74, such as first position 76. Source 14 is rotated in a circular orbit around Z-axis 72 such that a first quantity of views 78 is acquired at a first quantity of radiation source positions 80.

Radiation source 14 is translated along Z-axis 72 to another position 74, such as a second position 82 on Z-axis 72 different than first position 76. Radiation source 14 is again rotated in a circular orbit such that a second quantity of views 84 is acquired at a second quantity of radiation source positions 86, wherein second quantity of views 84 is one-half first quantity of views 78. Radiation source 14 is then translated to another position 74, such as a third position 90 on z-axis 72 different from first position 76 and second position 82 to acquire a third quantity of views 92 at a third quantity of radiation source positions 94 equivalent to first quantity of views 78.

In use, radiation source 14 is translated along Z-axis 72 to a first face 100 of a region of interest (ROI) 102. A quantity of views is acquired at each Z-axis position 74 until a second face 104 of ROI 102 is acquired. As shown the quantity of views for each circle 58 decreases by one-half from first face 100 until the views for a center-plane 106 are acquired. The quantity of views for each circle 58 then increase by a factor of two until the views for second face 104 have been acquired. The binary tree sampling pattern is symmetric with respect to center-plane 106. For example, if first face 100 and second face 104, i.e. the minimum and maximum Z-positions respectively, contain 1000 views, then next two circles 58 closer to center-plane 106 will contain 500 views, etc. Inner circles 58 can contain fewer views because points in these planes receive contributions from rays originating on other circles 58. As shown in FIG. 9 the pattern separates into circles 58 (or sets of constant Z-location), each with uniformly spaced angular samples that complement the contributions from adjacent circles 58.

Figure 10:
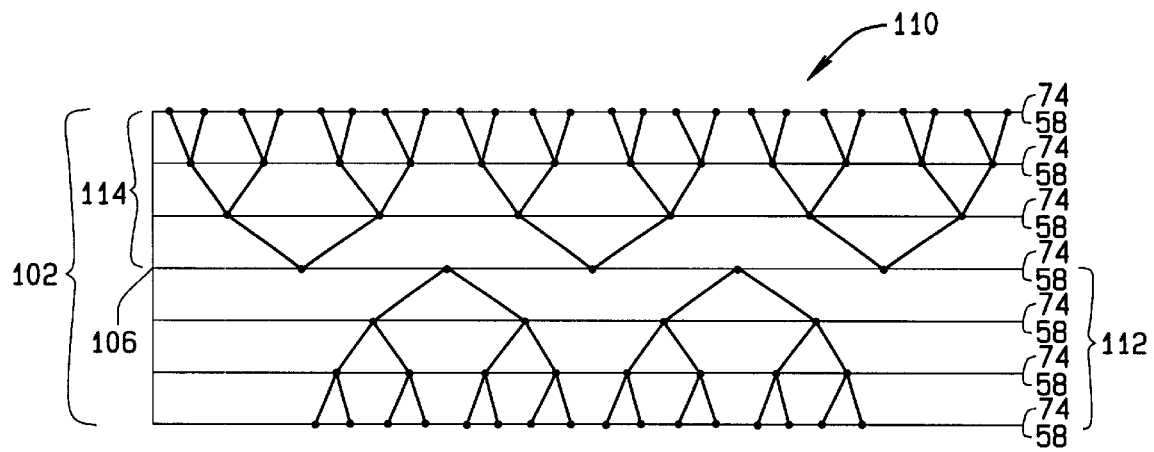
FIG. 10 is an illustration of an offset binary tree sampling pattern acquired using the method shown in FIG. 8.

FIG. 10 is an illustration of a offset binary tree sampling pattern 110 acquired using method 60. As shown, a lower set of views 112 can be offset from an upper set of views 114 to double the an angular sampling rate at the Z=0 plane, i.e. center-plane 106. The maximum number of views necessary to cover ROI 102 is 4*P, regardless of the number of Z-locations, i.e. positions 74, for the source point when using the offset binary tree sampling pattern. This is because P+P/2+P/4+. . . P/N=2*P, and the pattern is symmetric around center-plane 106. Therefore, the number of views needed is independent of the number of circles 58 used.

While the invention has been described in terms of various specific embodiments, those skilled in the art will recognize that the invention can be practiced with modification within the spirit and scope of the claims.

What is claimed is:

1. A method for acquiring views of an object, said method comprising:
   acquiring a first quantity of views at a first position on a z-axis;
   acquiring a second quantity of views different from the first quantity at a second position on the z-axis different from the first position; and
   acquiring a third quantity of views equivalent to the first quantity at a third position on the z-axis different from the first position and the second position.

2. A method in accordance with claim 1 wherein said acquiring a second quantity of views different from the first quantity at a second position on the z-axis different from the first position comprises acquiring a second quantity of views at a center-plane.

3. A method in accordance with claim 1 wherein said acquiring a second quantity of views different from the first quantity at a second position on the z-axis different from the first position comprises acquiring a second quantity of views that is one-half the first quantity.

4. A method in accordance with claim 1 wherein the first quantity of views, the second quantity of views, and the third quantity of views comprise a binary tree sampling pattern.

5. A method in accordance with claim 1 wherein the first quantity of views, the second quantity of views, and the third quantity of views comprise an offset binary tree sampling pattern.

6. A method in accordance with claim 1 wherein said method further comprises:
   rotating a radiation source in a first circle to acquire the first quantity of views;
   rotating the radiation source in a second circle to acquire the second quantity of views; and
   rotating the radiation source in a third circle to acquire the third quantity of views.

7. A method in accordance with claim 6 wherein said method further comprises acquiring the first quantity of views, the second quantity of views and the third quantity of views in accordance with:

$$\theta_k = \frac{2\pi k}{P}, \; z_k = a_1, \; 0 \leq k < P$$

$$\theta_k = \frac{2\pi(k-P)}{P}, \; z_k = a_2, \; P \leq k < 2P$$

$$\vdots$$

$$\theta_k = \frac{2\pi(k-(L-1)P)}{P},$$

$$z_k = a_L, \; (L-2)P \leq k < (L-1)P$$

where:
   k is a single view;
   l is a single circle acquired at a point z on the Z-axis
   L is a total quantity of circles acquired;
   $\theta_k$ is a source angle when acquiring view k;
   P is a quantity of views acquired for each source orbit;
   $z_k$ is a projection k acquired at a point z on the Z axis; and
   $a_n$ is a point on the Z axis, where n=1 . . . L.

8. A computer for acquiring views of an object, said computer programmed to:
   acquire a first quantity of views at a first position on a z-axis;
   acquire a second quantity of views different from the first quantity at a second position on the z-axis different from the first position; and
   acquire a third quantity of views equivalent to the first quantity at a third position on the z-axis different from the first position and the second position.

9. A computer in accordance with claim 8 wherein to acquire a second quantity of views different from the first quantity at a second position on the z-axis different from the first position, said computer further configured to acquire a second quantity of views at a center-plane.

10. A computer in accordance with claim 8 wherein to acquire a second quantity of views different from the first quantity at a second position on the z-axis different from the first position, said computer further configured to acquire a second quantity of views that is one-half the first quantity.

11. A computer in accordance with claim 8 wherein to acquire a first quantity of views, a second quantity of views, and a third quantity of views, said computer further configured to acquire less than approximately 4*P views of the object of interest.

12. A computer in accordance with claim 8 wherein said computer further configured to:
   rotate a radiation source in a first circle to acquire the first quantity of views;
   rotate the radiation source in a second circle to acquire the second quantity of views; and
   rotate the radiation source in a third circle to acquire the third quantity of views.

13. A computer in accordance with claim 12 wherein said computer further configured to acquire the first quantity of views, the second quantity of views and the third quantity of views in accordance with:

$$\theta_k = \frac{2\pi k}{P}, \ z_k = a_1, \ 0 \le k < P$$

$$\theta_k = \frac{2\pi (k - P)}{P}, \ z_k = a_2, \ P \le k < 2P$$

$$\vdots$$

$$\theta_k = \frac{2\pi (k - (L-1)P)}{P},$$

$$z_k = a_L, \ (L-2)P \le k < (L-1)P$$

where:
   k is a single view;
   l is a single circle acquired at a point z on the Z-axis
   L is a total quantity of circles acquired;
   $\theta_k$ is a source angle when acquiring view k;
   P is a quantity of views acquired for each source orbit;
   $z_k$ is a projection k acquired at a point z on the Z axis; and
   $a_n$ is a point on the Z axis, where n=1. . . L.

14. A computed tomographic (CT) imaging for acquiring views of an object, said CT system comprising:
   a detector array;
   at least one radiation source; and
   a computer coupled to said detector array and said radiation source, said computer configured to:
      acquire a first quantity of views at a first position on a z-axis;
      acquire a second quantity of views different from the first quantity at a second position on the z-axis different from the first position; and
      acquire a third quantity of views equivalent to the first quantity at a third position on the z-axis different from the first position and the second position.

15. A computer in accordance with claim 14 wherein to acquire a second quantity of views different from the first quantity at a second position on the z-axis different from the first position, said computer further configured to acquire a second quantity of views at a center-plane.

16. A computer in accordance with claim 14 wherein to acquire a second quantity of views different from the first quantity at a second position on the z-axis different from the first position, said computer further configured to acquire a second quantity of views that is one-half the first quantity.

17. A computer in accordance with claim 14 wherein to acquire a first quantity of views, a second quantity of views, and a third quantity of views, said computer further configured to acquire less than approximately 4*P views of the object of interest.

18. A computer in accordance with claim 14 wherein said computer further configured to:
   rotate a radiation source in a first circle to acquire the first quantity of views;
   rotate the radiation source in a second circle to acquire the second quantity of views; and
   rotate the radiation source in a third circle to acquire the third quantity of views.

19. A method in accordance with claim 12 wherein said computer further configured to acquire the first quantity of views, the second quantity of views and the third quantity of views in accordance with:

$$\theta_k = \frac{2\pi k}{P}, \ z_k = a_1, \ 0 \le k < P$$

$$\theta_k = \frac{2\pi (k - P)}{P}, \ z_k = a_2, \ P \le k < 2P$$

$$\vdots$$

$$\theta_k = \frac{2\pi (k - (L-1)P)}{P},$$

$$z_k = a_L, \ (L-2)P \le k < (L-1)P$$

where:
   k is a single view;
   l is a single circle acquired at a point z on the Z-axis
   L is a total quantity of circles acquired;
   $\theta_k$ is a source angle when acquiring view k;
   P is a quantity of views acquired for each source orbit;
   $z_k$ is a projection k acquired at a point z on the Z axis; and
   $a_n$ is a point on the Z axis, where n=1. . . L.

20. A computed tomographic (CT) imaging for reconstructing an image of an object, said CT system comprising:
   a detector array;
   at least one radiation source; and
   a computer coupled to said detector array and said radiation source, said computer configured to:
      divide a region of interest into a plurality of circles wherein each circle is positioned at a different position on the Z-axis;
      acquire a first quantity of views at a first position on a z-axis;
      acquire a second quantity of views that is one-half the first quantity of views, at a center-plane on the z-axis; and
      acquire a third quantity of views equivalent to the first quantity, at a third position on the z-axis different from the first position and the center-plane.

21. A method for reconstructing an image of an object, said method comprising:
   acquiring a plurality of circle trajectories wherein each circle trajectory includes a plurality of views; and
   generating a single reconstruction for each of the acquired circle trajectories.

22. A method in accordance with claim 21 further comprising combining the reconstructions using weights that vary as a function of a spatial coordinate.

23. A method in accordance with claim 21 wherein said generating a single reconstruction for each of the acquired circle trajectories comprises generating a single reconstruction using an FDK algorithm.

24. A method in accordance with claim 22 wherein said combining the reconstructions using weights that vary as a function of a spatial coordinate comprises combining the reconstructions using weights that vary as a function of a spatial coordinate according to:

$$f(x, y, z) = \sum_{1}^{L} w_l(x, y, z) f_l(x, y, z).$$

25. A method in accordance with claim 21 wherein said acquiring a plurality of circle trajectories wherein each circle trajectory includes a plurality of views comprises acquiring a plurality of circle trajectories equally spaced along a Z-axis in according to:

$$a_l = (l - L/2) \cdot \Delta z$$

where l is an single circle;

L is a quantity of l circles; and $\Delta z$ is a change in the Z-axis position.

26. A method in accordance with claim 22 wherein said combining the reconstructions using weights that vary as a function of a spatial coordinate comprises combining the reconstructions according to:

$$f(x, y, z) = \sum_{l=1}^{L} w(z - (l - L/2) \cdot \Delta z) f_l(x, y, z)$$

l is an single circle;

$f_l(x, y, z)$ is a single circle trajectory;

L is a quantity of l circles;

w is a weighting function;

z is a Z-axis position; and $\Delta z$ is a change in the Z-axis position.

27. A method in accordance with claim 22 wherein said combining the reconstructions using weights comprises combining the reconstructions using weights that satisfy an interpolation property according to:

$$w(z) = \begin{cases} 1 & z = 0 \\ 0 & z = (l - L/2) \cdot \Delta a, l = 0 \ldots L - 1 \end{cases}.$$

* * * * *